US009724215B2

(12) United States Patent
Tippett et al.

(10) Patent No.: US 9,724,215 B2
(45) Date of Patent: Aug. 8, 2017

(54) STENT

(71) Applicant: evYsio Medical Devices ULC, Vancouver (CA)

(72) Inventors: Jonathan G. Tippett, Vancouver (CA); Martina Wan, Vancouver (CA); Ian McDougall, North Vancouver (CA)

(73) Assignee: evYsio Medical Devices ULC, Vancouver (CA)

( * ) Notice: Subject to any disclaimer, the term of this patent is extended or adjusted under 35 U.S.C. 154(b) by 0 days.

(21) Appl. No.: 14/755,513

(22) Filed: Jun. 30, 2015

(65) Prior Publication Data
US 2015/0297377 A1    Oct. 22, 2015

Related U.S. Application Data

(63) Continuation of application No. 12/704,932, filed on Feb. 12, 2010, now Pat. No. 9,101,504.
(Continued)

(51) Int. Cl.
*A61F 2/82* (2013.01)
*A61F 2/915* (2013.01)
*A61F 2/91* (2013.01)

(52) U.S. Cl.
CPC ............ *A61F 2/915* (2013.01); *A61F 2/82* (2013.01); *A61F 2/91* (2013.01);
(Continued)

(58) Field of Classification Search
CPC .................................................. A61F 2/82
See application file for complete search history.

(56) References Cited

U.S. PATENT DOCUMENTS 6,066,169 A    5/2000   McGuinness
6,629,994 B2  10/2003  Gomez et al.
(Continued)

FOREIGN PATENT DOCUMENTS

CA    2548566 A1    8/2005
CN    1331957 A     1/2002
(Continued)

OTHER PUBLICATIONS

The Third Office Action for Chinese Patent Application No. 201080006940.1 with a mailing date of Jul. 29, 2015.
(Continued)

*Primary Examiner* — Matthew Schall
(74) *Attorney, Agent, or Firm* — Katten Muchin Rosenman LLP

(57) ABSTRACT

A stent comprises a plurality of undulating circumferential portions, each circumferential portion comprising alternating peaks and valleys; and a plurality of longitudinally extending portions connecting the plurality of undulating circumferential portions. Each of the plurality of longitudinally extending portions contains a first longitudinally extending strut and a second longitudinally extending strut circumferentially offset with respect to the first longitudinally extending strut. The first longitudinally extending strut and the second longitudinally extending strut are interconnected by a connecting portion. Circumferentially adjacent first longitudinally extending struts in a pair of circumferentially adjacent longitudinally extending portions are circumferentially spaced at a first distance and circumferentially adjacent second longitudinally extending struts in the pair of circumferentially adjacent longitudinally extending portions are circumferentially spaced at a second distance. The first distance is greater than the second distance. The present stent has a very desirable balance of conformability
(Continued)

and flexibility while obviating or mitigating crashing, out of tubular configuration and other problems (as discussed herein).

20 Claims, 12 Drawing Sheets

Related U.S. Application Data

(60) Provisional application No. 61/202,239, filed on Feb. 9, 2009.

(52) U.S. Cl.
CPC ............... *A61F 2002/91558* (2013.01); *A61F 2002/91575* (2013.01); *A61F 2220/0075* (2013.01)

(56) References Cited

U.S. PATENT DOCUMENTS

| | | | |
|---|---|---|---|
| 6,955,686 | B2 | 10/2005 | Majercak et al. |
| 7,025,777 | B2 | 4/2006 | Moore |
| 7,357,813 | B2 | 4/2008 | Burgermeister |
| 7,645,297 | B2 | 1/2010 | Nissl |
| 7,651,524 | B2 | 1/2010 | Moriuchi et al. |
| 2004/0002753 | A1 | 1/2004 | Burgermeister et al. |
| 2006/0200229 | A1 | 9/2006 | Burgermeister et al. |
| 2007/0021827 | A1 | 1/2007 | Lowe et al. |

FOREIGN PATENT DOCUMENTS

| | | |
|---|---|---|
| CN | 1688264 A | 10/2005 |
| WO | 2004/010902 A1 | 2/2004 |
| WO | 2004/091428 A2 | 10/2004 |
| WO | 2005/009294 A1 | 2/2005 |

OTHER PUBLICATIONS

Office Action for Russian Patent Application No. 2011128776/02(042544) with a mailing date of Feb. 7, 2014.
International Search Report for International Application No. PCT/CA2010/000170 with a mailing date of Jun. 2, 2010.
Office Action for Canadian Patent Application No. 2,750,228 with a mailing date of Nov. 26, 2013.
First Office action for Chinese Patent Application No. 201080006940.1 with a mailing date of Oct. 11, 2013.
Office Action for Israeli Patent Application No. 214053 with a mailing date of Apr. 29, 2013 and an excerpt from a letter from Reinhold and Cohn that gives a summary of the office action in English.
Patent Examination Report No. 1 for Australian Patent Application No. 201021075 with a mailing date of Nov. 19, 2014.
The Second Office Action for Chinese Patent Application No. 201080006940.1 with a mailing date of Dec. 23, 2014.
The First Office Action for Japanese Patent Application No. 2011-548511 with a mailing date of Feb. 4, 2014.

PRIOR ART

PRIOR ART

PRIOR ART

PRIOR ART

PRIOR ART

Fig.10 tension
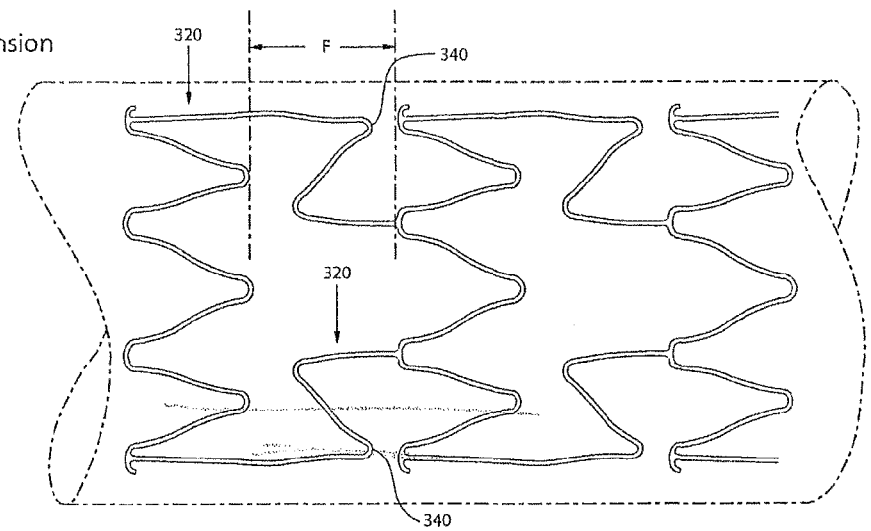
Fig.11 neutral
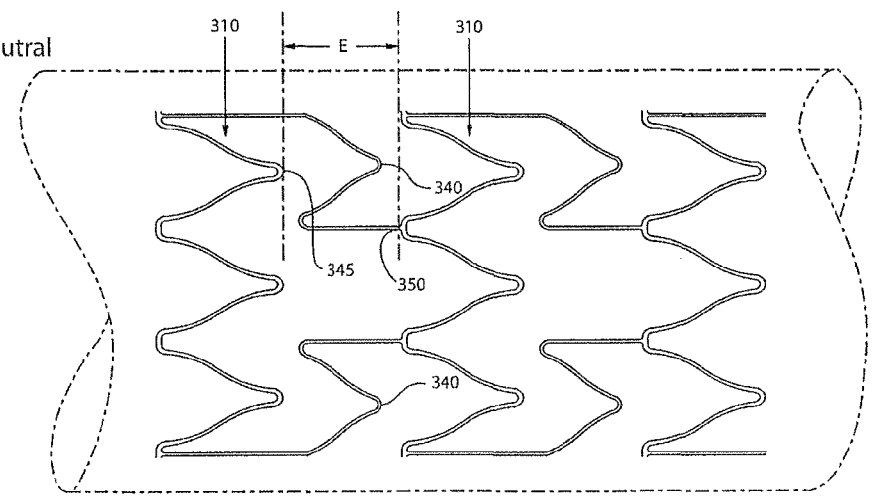
Fig.12 compression
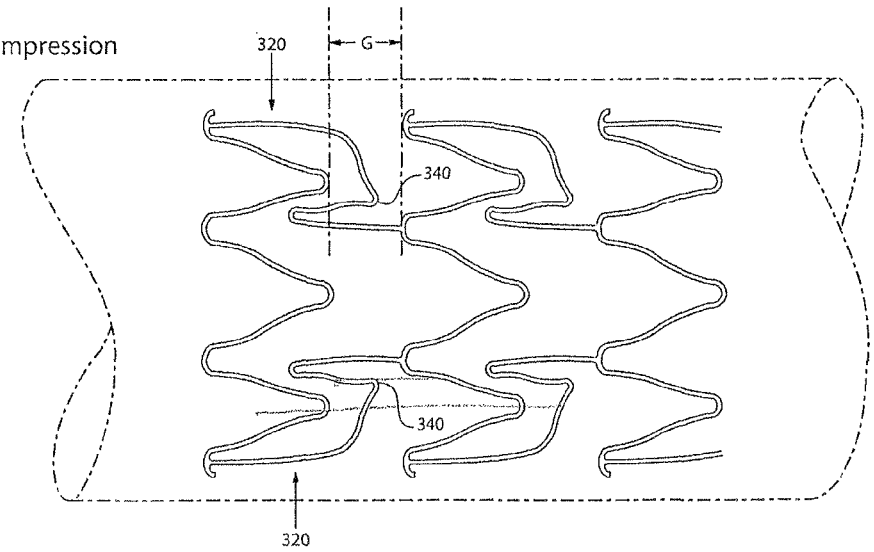

Fig.16
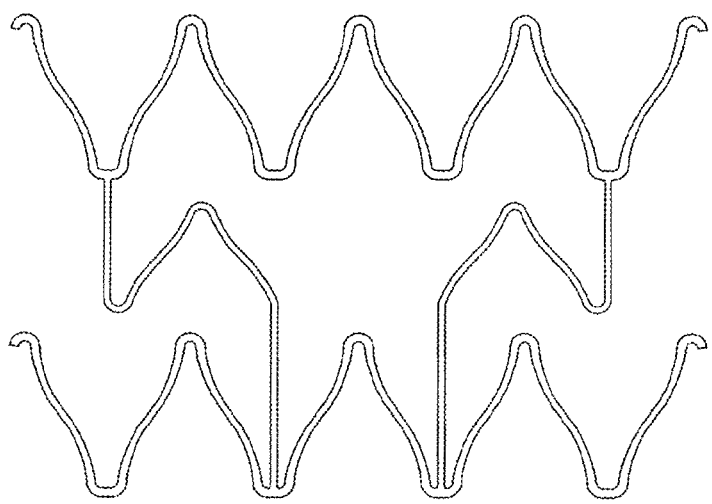 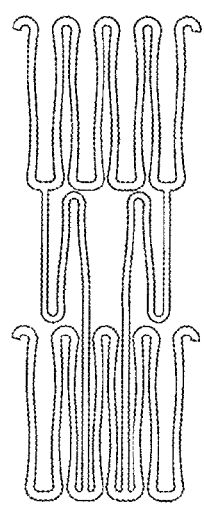
(a) expanded　　　　　　　　　(b) crimped

STENT

CROSS-REFERENCE TO RELATED APPLICATION

This application is a continuation of U.S. patent application Ser. No. 12/704,932, filed Feb. 12, 2010, which claims the benefit under 35 U.S.C. §119(e) of U.S. Patent Appln. No. 61/202,239, filed Feb. 9, 2009, the contents of both hereby incorporated by reference.

BACKGROUND OF THE INVENTION

Field of the Invention

The present invention relates to an expandable stent.

Description of the Prior Art

Stents are generally known. Indeed, the term "stent" has been used interchangeably with terms such as "intraluminal vascular graft" and "expansible prosthesis". As used throughout this specification the term "stent" is intended to have a broad meaning and encompasses any expandable prosthetic device for implantation in a body passageway (e.g., a lumen or artery).

In the late 1980's, the use of stents attracted an increasing amount of attention due the potential of these devices to be used, in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g. natural or iatrogenic) within the human body and can include a member selected from the group comprising: blood vessels, respiratory ducts, gastrointestinal ducts and the like.

First generation stents were self-expanding, spring-like devices which were inserted in the body passageway in a contracted state. When released, the stent would automatically expand and increase to a final diameter dependent on the size of the stent and the elasticity of the body passageway. An example of such a stent is known in the art as the Wallstent™.

The self-expanding stents were found by some investigators to be deficient since, when deployed, they could place undue, permanent stress on the walls of the body passageway. Further, upon expansion, the stent would shorten in length in an unpredictable fashion thereby reducing the reliability of the stent. This led to the development of various stents which were controllably expandable at the target body passageway so that only sufficient force to maintain the patency of the body passageway was applied in expanding the stent—i.e., the so-called "balloon expandable stents".

Generally, in these second generation systems, a stent, in association with a balloon, is delivered to the target area of the body passageway by a catheter system. Once the stent has been properly located (for example, for intravascular implantation the target area of the vessel can be filled with a contrast medium to facilitate visualization during fluoroscopy), the balloon is expanded, thereby expanding the stent by plastic deformation so that the latter is urged in place against the body passageway. As indicated above, the amount of force applied is at least that necessary to maintain the patency of the body passageway. At this point, the balloon is deflated and withdrawn within the catheter, and subsequently removed. Ideally, the stent will remain in place and maintain the target area of the body passageway substantially free of blockage (or narrowing).

A balloon-expandable stent which gained some notoriety in the art in the 1990's was known as the Palmaz-Schatz™ stent. This stent is discussed in a number of patents including U.S. Pat. Nos. 4,733,665, 4,739,762, 5,102,417 and 5,316,023.

Another stent which has gained some notoriety in the art in the 1990's was known as the Gianturco-Roubin Flex-Stent. This stent is discussed in a number of patents, including U.S. Pat. Nos. 4,800,882, 4,907,336 and 5,041,126.

Other types of stents are disclosed in the following patents:

U.S. Pat. No. 5,035,706 (Gianturco et al.),
U.S. Pat. No. 5,037,392 (Hillstead),
U.S. Pat. No. 5,147,385 (Beck et al.),
U.S. Pat. No. 5,282,824 (Gianturco),
Canadian patent 1,239,755 (Wallsten), and
Canadian patent 1,245,527 (Gianturco et al.).

While these prior art stents have achieved a varying degree of success, the art is constantly in need of new stents having improved flexibility and stability while being able to be readily implanted with little or no trauma to the target lumen. It would be highly desirably if such new stents additionally were relatively resistant to kinking during bending while maintaining wall apposition and side branch access (particularly important when deploying the stent in the aorta).

SUMMARY OF THE INVENTION

It is an object of the present invention to obviate or mitigate at least one of the above-mentioned disadvantages of the prior art.

It is another object of the present invention to provide a novel stent comprising, in two dimensions:

a plurality of undulating circumferential portions, each circumferential portion comprising alternating peaks and valleys; and a plurality of longitudinally extending portions connecting the plurality of undulating circumferential portions;

wherein:

(i) each of the plurality of longitudinally extending portions comprising a first longitudinally extending strut and a second longitudinally extending strut circumferentially offset with respect to the first longitudinally extending strut, the first longitudinally extending strut and the second longitudinally extending strut being interconnected by a connecting portion; and (ii) a pair of circumferentially adjacent first longitudinally extending struts in a pair of circumferentially adjacent longitudinally extending portions are circumferentially spaced at a first distance and circumferentially adjacent second longitudinally extending struts in the pair of circumferentially adjacent longitudinally extending portions are circumferentially spaced at a second distance, the first distance being greater than the second distance.

Thus, the present inventors have discovered a novel stent design which provides a very desirable balance between conformability while obviating or mitigating the disadvantages associated with crashing and out of tubular configuration that will be described below. Additionally, the present stent is relatively resistant to kinking during bending while maintaining good wall apposition and desirable side branch access. It is believed that these advantages accrue from the design of the longitudinal connector used to interconnect circumferential rings in the present stent, together with the orientation of circumferentially adjacent pairs of these longitudinal connectors. This will be described in more detail below.

While a specifically preferred embodiment of the present stent will be described below with reference to the drawings, the present stent may include one or more of the following features:

- the connecting portion that connects two longitudinally extending struts may comprise at least one apex (i.e., one or more apices);
- a pair of the circumferentially adjacent longitudinally extending portions in two dimensions, may be configured to be substantially mirror images of one another along a longitudinal axis of the stent;
- a pair of the circumferentially adjacent longitudinally extending portions, in two dimensions, may be configured to be substantially non-superimposable mirror images of one another along a longitudinal axis of the stent;
- the section of first undulating circumferential portion between two ends of adjacent longitudinally extending portions connecting to a first undulating circumferential portion and the section of the second undulating circumferential portion between the other ends of the same two longitudinally extending portions to a second undulating circumferential portion adjacent to the first undulating circumferential portion, the first section and the second section having an equivalent number of peaks and valleys;
- the section of first undulating circumferential portion between two ends of adjacent longitudinally extending portions connecting to a first undulating circumferential portion and the section of the second undulating circumferential portion between the other ends of the same two longitudinally extending portions connecting to a second undulating circumferential portion adjacent to the first undulating circumferential portion, the first section and the second section having a different number of peaks and valleys;
- an adjacent pair of undulating circumferential portions may comprises an equivalent number of peaks and valleys;
- an adjacent pair of undulating circumferential portion may comprise a different number of peaks and valleys;
- the first longitudinally extending strut may comprise a straight portion;
- the second longitudinally extending strut may comprise a straight portion;
- each of the first longitudinally extending strut and the second longitudinally extending strut may comprise a straight portion;
- the first longitudinally extending strut may comprise a curvilinear portion;
- the second longitudinally extending strut may comprise a curvilinear portion;
- each of the first longitudinally extending strut and the second longitudinally extending strut may comprise a curvilinear portion;
- the first longitudinally extending strut may comprise a curved portion;
- the second longitudinally extending strut may comprise a curved portion;
- each of the first longitudinally extending strut and the second longitudinally extending strut may comprise a curved portion;
- the connecting portion may comprise a first strut segment connected to the first longitudinally extending strut and a second strut segment connected to the second longitudinally extending strut;
- the first strut segment and the second strut segment may be interconnected to define at least one apex;
- the first strut portion may comprise a straight portion;
- the second strut portion may comprise a straight portion;
- each of the first strut portion and the second strut portion may comprise a straight portion;
- the first strut portion may comprise a curved portion;
- the second strut portion may comprises a curved portion;
- each of the first strut portion and the second strut portion may comprise a curved portion;
- the first strut portion may comprise a curvilinear portion;
- the second strut portion may comprise a curvilinear portion;
- each of the first strut portion and the second strut portion may comprise a curvilinear portion;
- the at least one apex may comprise a curved portion;
- the at least one apex may comprise a straight portion;
- the at least one apex may comprise a pointed portion;
- the first strut portion and the second strut portion may be substantially mirror images of one another along a longitudinal axis of the stent;
- the first strut portion and the second strut portion may be non-mirror images of one another along a longitudinal axis of the stent;
- the first longitudinally extending strut may be connected to a valley of a first undulating circumferential portion and the second longitudinally extending strut may be connected to a peak of a second undulating circumferential portion adjacent to the first undulating circumferential portion;
- the first longitudinally extending strut may be connected to a peak of a first undulating circumferential portion and the second longitudinally extending strut may be connected to a peak of a second undulating circumferential portion adjacent to the first undulating circumferential portion;
- the first longitudinally extending strut may be connected to a valley of a first undulating circumferential portion and the second longitudinally extending strut may be connected to a valley of a second undulating circumferential portion adjacent to the first undulating circumferential portion;
- the first longitudinally extending strut may be connected to a first connection point intermediate a peak and a valley of a first undulating circumferential portion and the second longitudinally extending strut may be connected to a second connection point intermediate to a peak and a valley of a second undulating circumferential portion adjacent to the first undulating circumferential portion;
- the first longitudinally extending strut may be connected to a first connection point that is substantially midway between a peak and a valley of a first undulating circumferential portion and the second longitudinally extending strut may be connected to a second connection point that is substantially midway between a peak and a valley of a second undulating circumferential portion adjacent to the first undulating circumferential portion;
- the stent may comprise an even number of longitudinally extending portions interconnecting adjacent circumferential portions;

ratio of the number peaks in each of an adjacent pair of circumferential portions to the number of longitudinally extending portions connecting the pair is 2:1;

the stent may contain 4 longitudinally extending portions interconnecting an adjacent pair of circumferential portions;

each of the pair of circumferential portions have 8 peaks;

the stent may have a diameter of less than or equal to about 30 mm;

the stent may contain 6 longitudinally extending portions interconnecting an adjacent pair of circumferential portions;

each of the pair of circumferential portions may have 12 peaks;

the stent may have a diameter of greater than about 30 mm.

the stent may contain 8 longitudinally extending portions interconnecting an adjacent pair of circumferential portions;

the stent may contain 12 longitudinally extending portions interconnecting an adjacent pair of circumferential portions;

the stent may be a balloon expandable material;

the stent may be constructed from a shape memory alloy;

the stent may be configured to be self-expanding;

the stent may be constructed from nitinol;

the stent may be constructed from a material selected from the group consisting of stainless steel, titanium, tantalum, nitinol, Elgiloy, NP35N and cobalt-chromium alloy;

the stent may be constructed from a non-metallic material;

the stent may be constructed from a biodegradable material; and/or the stent may be constructed from a bio-absorbable material.

BRIEF DESCRIPTION OF THE DRAWINGS

Embodiments of the present invention will be described with reference to the accompanying drawings, wherein like reference numerals denote like parts, and in which:

FIGS. 10-12 illustrate the stent design shown in FIGS. 7-9 under various stresses;

FIG. 16 illustrates a portion of the two dimensional representation of the stent of the present invention in an expanded (a) and a crimped (b) state.

With respect to FIGS. 2, 3, 5-7 and 9, it is noted that these drawings illustrate actual products. Of these, FIGS. 2, 3, 5, 6 and 9 illustrate a stent product in a bent configuration. In order to facilitate understanding what is illustrated, it should be noted that half of the product along its longitudinal axis (i.e., 180° is actually immersed in an opaque liquid (e.g., paint) so that what is actually shown is the product spanning approximately 180°. This protocol avoids complicating the illustrated view with the struts from the rear portion of the product (see, for example, FIG. 7 in which the entire product is illustrated).

DETAILED DESCRIPTION OF THE PREFERRED EMBODIMENTS

Prior to discussing the preferred embodiments of the present stent, a discussion of the problems with prior art stents will be discussed with reference to FIGS. 1-6.

Figure 1:
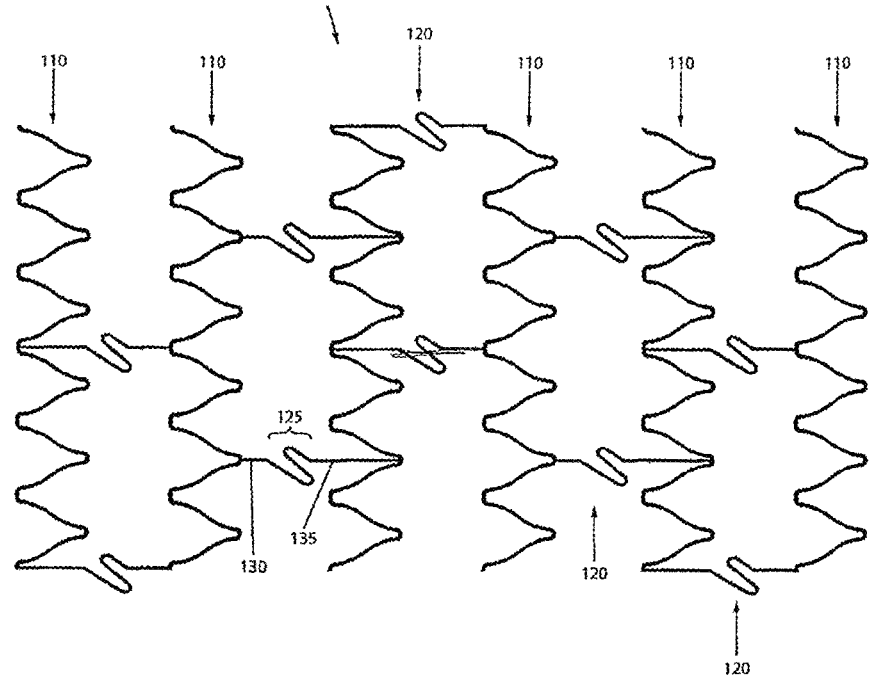
FIG. 1 illustrates a stent design, in two dimensions, that is outside the scope of the present invention.

With reference to FIG. 1, there is illustrated a two dimensional representation of a stent 100. By two dimensional representation, is meant a view of the stent as obtained by taking a tubular form of the stent, cutting it in a longitudinal direction and laying open/flattening the stent.

Stent 100 consists of a series of circumferential rings 110. In the illustrated embodiment, there are six circumferential rings 110.

Circumferential rings 110 are interconnected by longitudinal connectors 120. In the illustrated embodiment, there are two longitudinal connectors that interconnect each pair of circumferential rings 120.

Each longitudinal connector 120 consists of a flex member 125 that is disposed between a pair of straight sections 130, 135. Such longitudinal connectors are conventional in the art.

The stent design shown in FIG. 1 may be regarded as a so-called "peak-to-valley" design. By this it is meant that longitudinal connector 120 connects a peak of circumferential ring 110 with a valley of an adjacent circumferential ring 110. In general, peak-to-valley designs are known in the art.

When stent 100 is bent, a number of problems are encountered.

Figure 2:
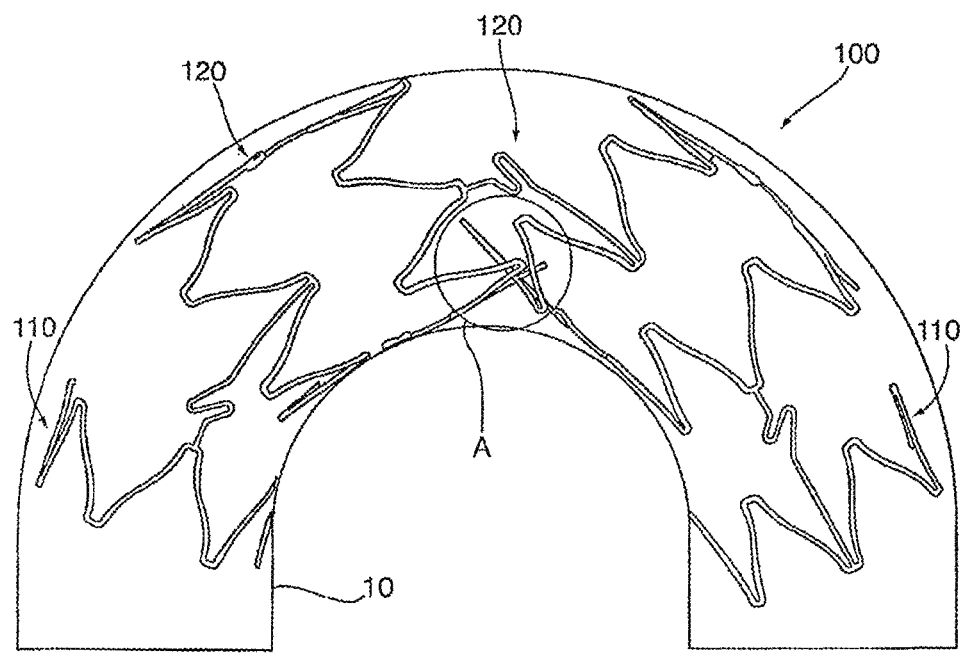
FIGS. 2 and 3, illustrate a stent shown in FIG. 1 in a bent configuration.

With reference to FIG. 2, stent 100 is shown in a bent state—this bent stent configuration is consistent with the type of bending often encountered during clinical use of stent 100. As illustrated, a problem results in that various of circumferential rings 110 contact or "crash" on the adjacent circumferential ring 110. For clarity, this is illustrated by circles A. As illustrated, during "crashing", the crowns (peaks) of adjacent circumferential rings contact each other and overlap and/or kink. This can create significant problems for the physician trying to implant stent 100. If the stent is to be implanted in a curved lumen, "crashing" results in interruption of blood flow and increased risk of thrombosis. Even if the stent is to be implanted elsewhere in the body (e.g., a relatively straight body lumen), if adjacent circumferential rings kink and become entangled, there is a risk that they will not untangle thereby compromising the ability of the stent to return to a proper straight configuration.

Further, while the bent configuration shown in FIG. 2 allows stent 100 generally to maintain its tubular configuration, the crashing of adjacent pairs of circumferential rings 110 adversely affects the flexibility of the stent and, can cause tangling of the crowns that in some cases, can result in damage to the stent. Tangling (resulting from "crashing") of adjacent pairs of circumferential rings in the stent can also lead to the circumferential rings being out of axial alignment. If this is not noticed by the physician, it can lead to potentially disastrous results for the patient as a result of fracture, strut protrusion through artery wall, increased risk of embolism/thrombosis.

Figure 3:
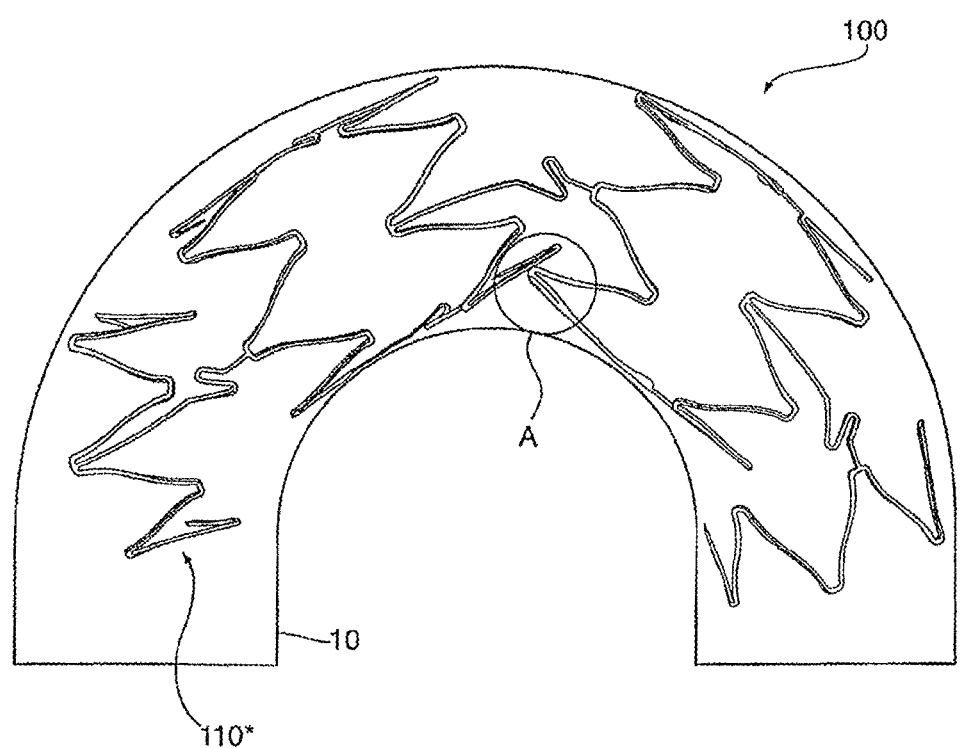

A more significant clinical problem with stent 100 can be seen with reference to FIG. 3. Here, stent 100 is shown in a bent state in an artery 10. As was seen in FIG. 2, in this configuration, there is crashing of adjacent circumferential rings 110 (see circles A). In addition, a further problem can be seen. Specifically, circumferential ring 110* actually rotates out of the tubular configuration to be in alignment with the longitudinal axis of the stent. This is clearly not an acceptable configuration of the stent and it cannot be correctly implanted in a safe manner when such a problem occurs. This problem is even more likely to occur clinically than "crashing" discussed above. When the problem does occur, it will not necessarily self-correct and, in most cases, would require some sort of intervention (possibility surgery) to remove an incorrectly implanted stent. In many cases, this exposes the patient to the very risk that was intended to be avoided by attempting an endovascular intervention.

Thus, while stent 100 illustrated in FIGS. 1-3 is very flexible, this high degree of flexibility appears to give rise to the crashing problem (FIGS. 2 and 3) and the "out of tubular configuration" problem (FIG. 3).

Figure 4:
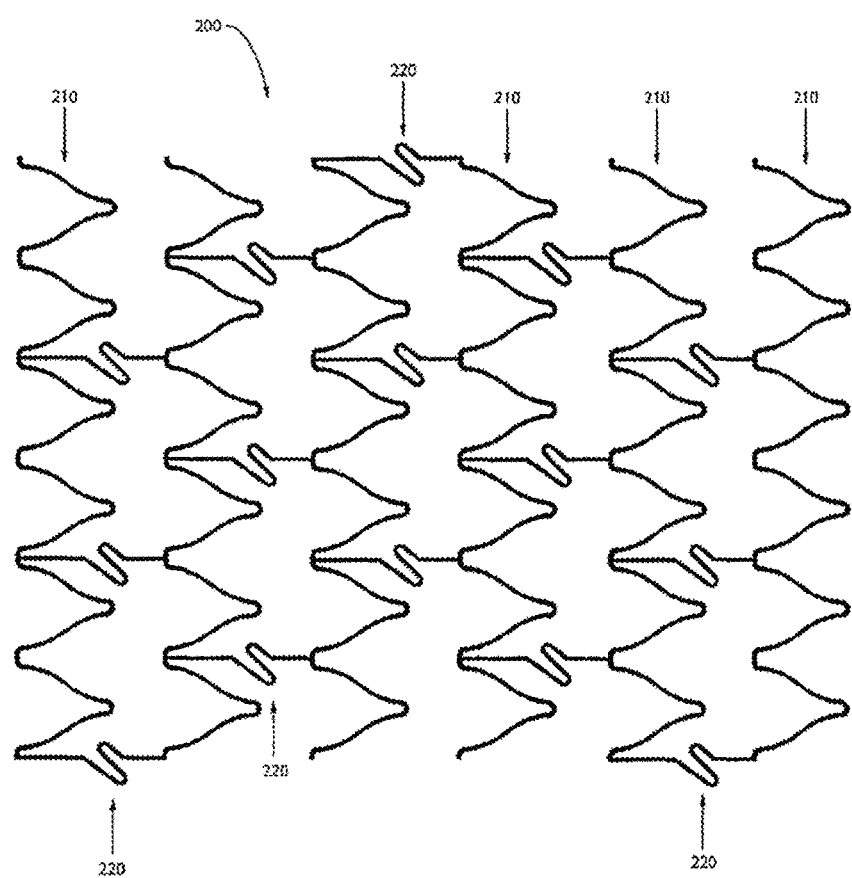
FIG. 4 illustrates a further stent design that is outside the scope of the present invention.

To overcome this problem, one could attempt to increase the number of longitudinal connectors used to connect each adjacent pair of circumferential rings—such a design is illustrated in FIG. 4.

Thus, in FIG. 4, there is illustrated a stent 200 having six circumferential rings 210. Circumferential rings 210 are similar to circumferential rings 110 in FIGS. 1-3. A series of longitudinal connectors 220 interconnect adjacent pairs of circumferential rings 210.

The difference between the stent designs in FIGS. 1-3 and that in FIG. 4 is that there are two longitudinal connectors 120 connecting each pair of circumferential rings 110 in stent 100 shown in FIGS. 1-3. In contrast, there are three longitudinal connectors 220 interconnecting each pair of circumferential rings 210 in stent 200 shown in FIG. 4.

Figure 5:
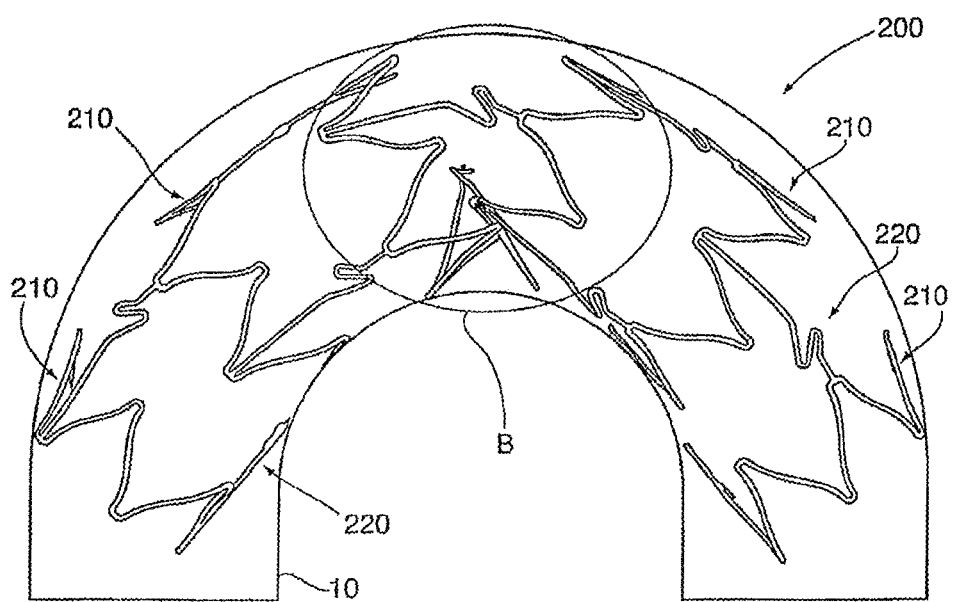
FIG. 5 illustrates the stent shown in FIG. 4 in a bent configuration.

The result of adding an additional longitudinal connector 220 is significant. As shown in FIG. 5, when stent 200 is bent, the "crashing" problem and the "out of tubular configuration" problem seen with stent 100 in FIGS. 1-3 is overcome. However, this comes at a cost of flexibility of stent 200. As can be seen in FIG. 5, when stent 200 is bent, the portion of the stent which forms the apex of the inner bend is susceptible to kinks—this is shown in circle B in FIG. 5. This problem results due to the less flexible nature of stent 200. For example, it can be seen in FIG. 5 that there is very little uniform bending of stent 200. Rather, it appears that most of the bending forces are concentrated in the region of stent 200 shown in circle B. To achieve bending of stent 200 high force is typically needed. Thus, there can be too much stress applied to the artery leading to clinical complications such as dissection, rupture or other acute/chronic injury to the artery. Further, there is a risk of flexure fatigue failure associated with the region of stent 200 shown in circle B. Still further, there is excessive protrusion of elements of the region of stent 200 shown in circle B leading to an increased risk of thrombosis and/or limitation/denial of access to the distal portion of the lumen in which stent 200 is implanted.

This results in a compromise in the conformability of the stent. As is known in the art, "conformability" refers to the ability of the stent to conform to the shape of the vessel as opposed to forcing the vessel to conform to the shape of the stent. In summary, there is a problem on the one hand of great flexibility but crashing/out of tubular configuration associated with the stent shown in FIGS. 1-3 while, on the other hand, there is the problem with kinking and lack of conformability associated with the stent shown in FIGS. 4-5. At least with respect to the stents illustrated in FIGS. 1-5, these problems depend on whether there are two or three longitudinal connectors interconnecting adjacent circumferential rings.

Figure 6:
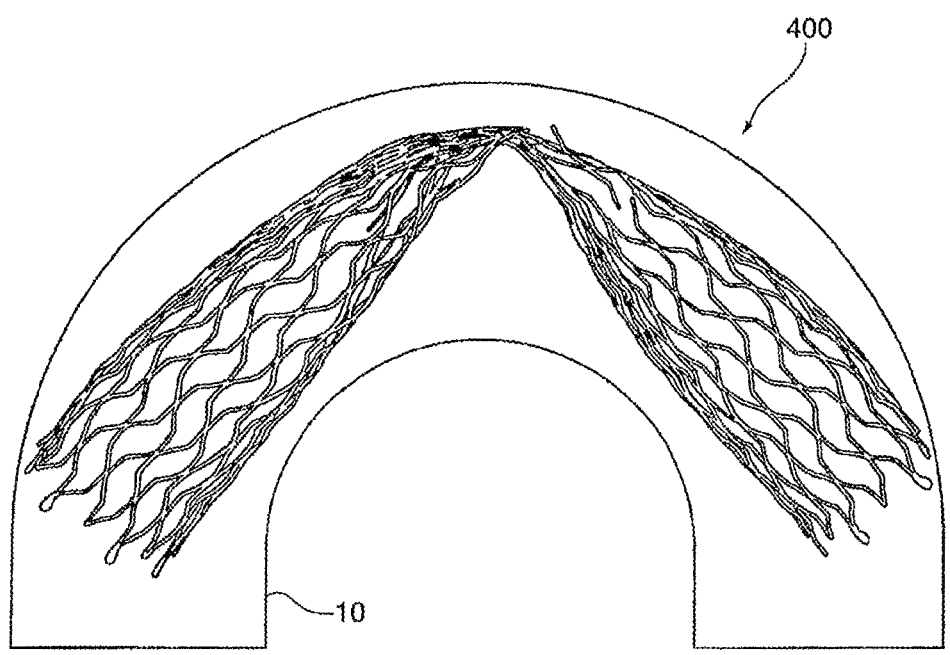
FIG. 6 illustrates a stent product commercially available from OptiMed under the tradename "Sinus-XL stent" in a bent configuration.

With reference to FIG. 6, there is illustrated a stent 400 shown in a bent state—this bent state is similar to the described above with reference to FIGS. 2, 3 and 5 described above. Stent 400 is a stent product commercially available from OptiMed under the tradename "Sinus-XL stent" and is often implanted by a physician in the aorta of a patient, typically in a straight portion of that lumen. This stent is not well suited for delivery and/or implantation through/in a curved lumen. Specifically, the "Instructions For Use" contained with the product include the following statements:

"The sinus XL stent is marked by its inflexible sinus wave structure. Thus, it must not be implanted at a joint or nearby a joint or in case of severe vessel/lumen curvatures."

The reason for this cautionary instruction is apparent with reference to FIG. 6 which illustrates the Sinus-XL stent in a bent configuration. As shown, there is significant kinking of stent 400 in the apex region of the bend and, after repeated bending, various struts in the device actually fractured. As is further apparent, the relatively tight porous pattern of the device when placed across a branch artery raises the risk of compromising the access to the side branch it is covering—this is particularly problematic if the stent is implanted in the aorta and crosses various of the arteries branching off the aorta. In such a case, the physician is likely blocked from access to the covered arteries (know in the art as being "jailed in" and the like), thus preventing the interventional treatment of that artery in the future.

Thus, there does remain a need in the art for a stent design which has an improved balance between flexibility and conformability without causing problems associated with crashing and out of tubular configuration described above. It would be particularly advantageous if these attributes of the stent did not compromise the crimpability of the stent. It would be further particularly advantageous if the stent was relatively resistant to kinking during bending while maintaining good wall apposition and desirable side branch access.

Figure 7:
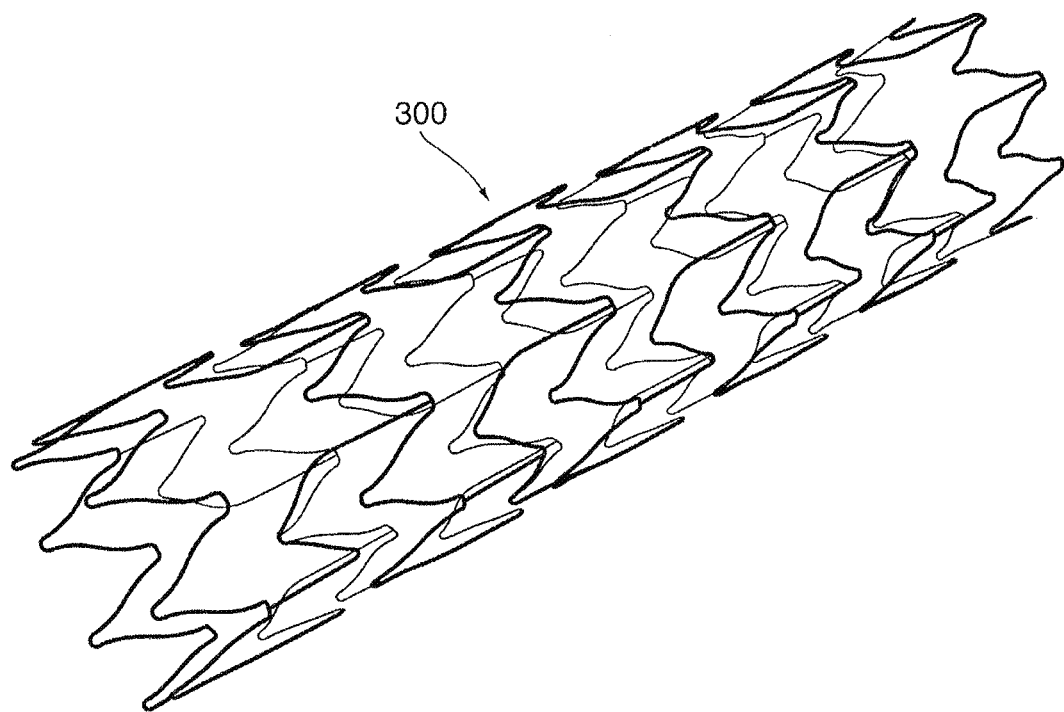
FIG. 7 illustrates a perspective view of a preferred embodiment of a stent in accordance with the present invention.

With reference to FIGS. 7-12, there is illustrated a stent 300 which accords with the preferred embodiment of the present invention. In FIG. 7 stent 300 is shown in an expanded state.

Figure 8:
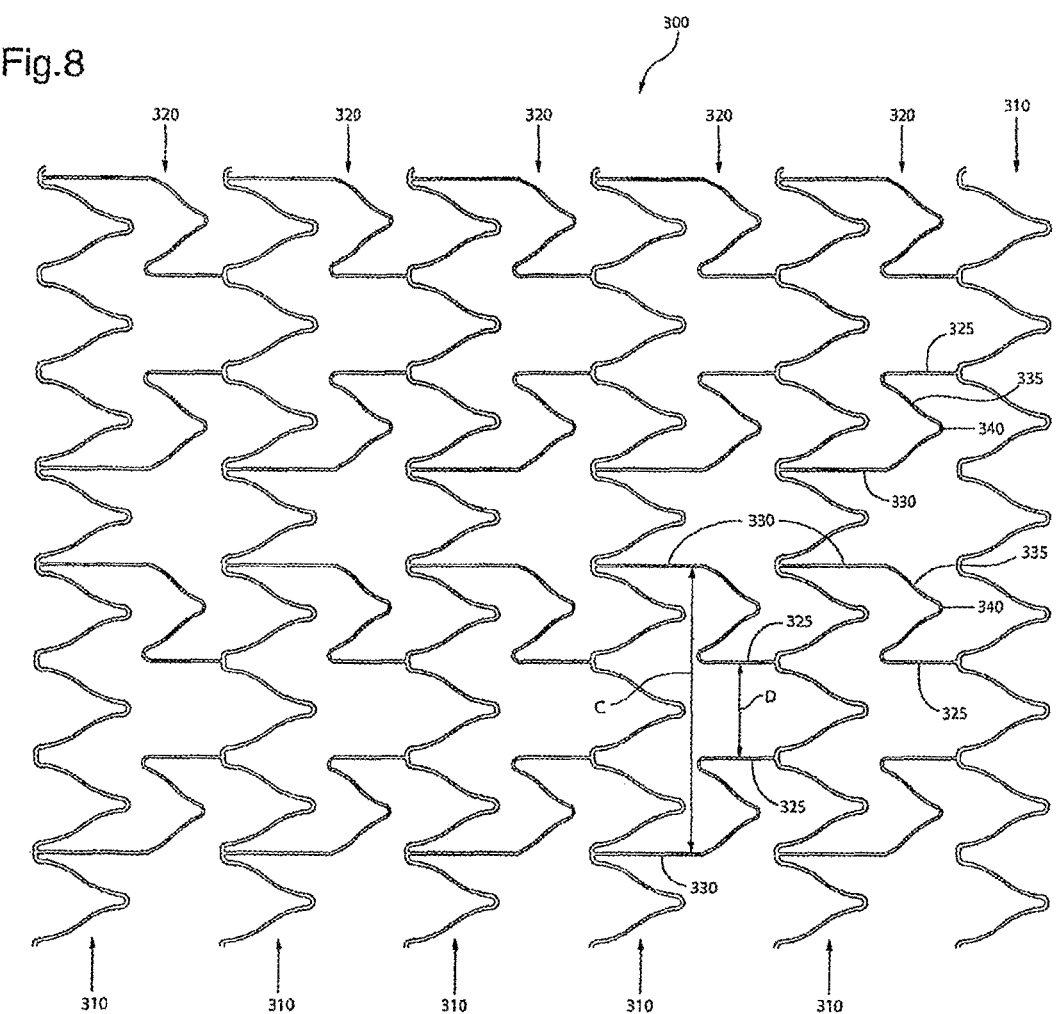
FIG. 8 illustrates the stent shown in FIG. 7 in a two dimensional representation.
Figure 9:
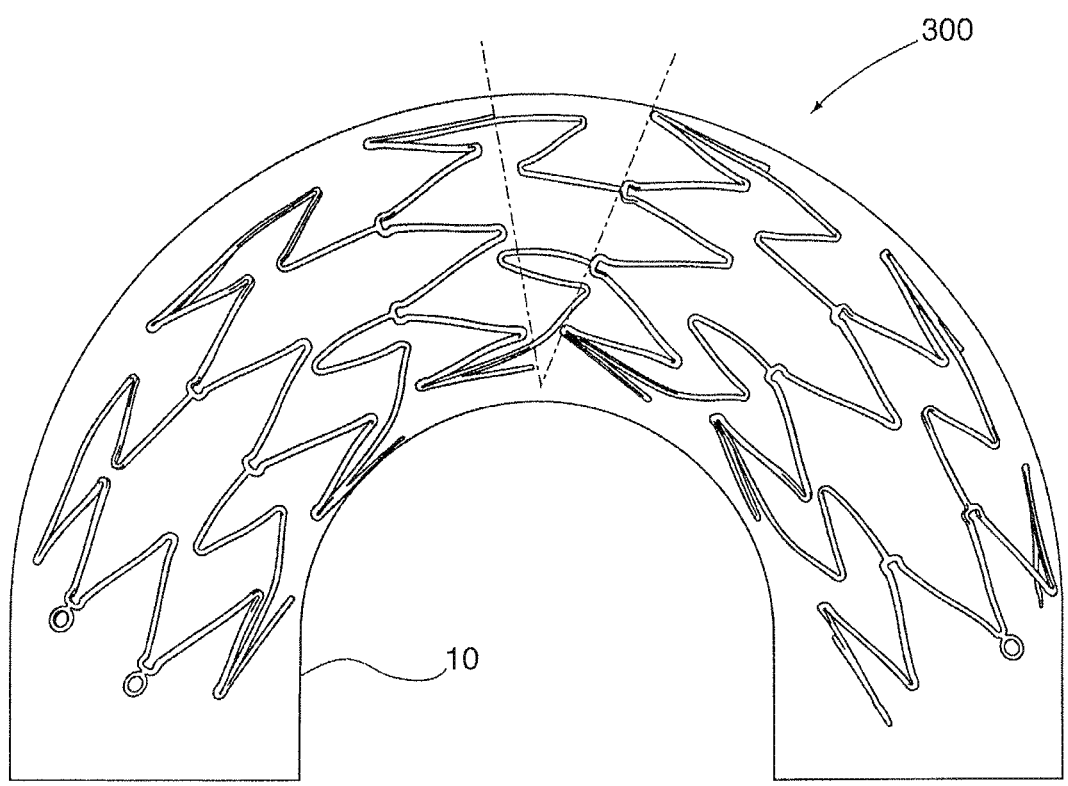
FIG. 9 illustrates the stent design shown in FIGS. 7 and 8 in a bent configuration.

As seen in FIG. 8, in two dimensions, stent 300 consists of a series of circumferential rings 310. Adjacent pairs of circumferential rings 310 are interconnected by a series of longitudinally extending portions 320. In the illustrated embodiment, there are four longitudinally extending portions 320 that interconnect with each pair of circumferential rings 310.

Each longitudinally extending portion 320 consists of a pair of longitudinally extending struts 325, 330. In each longitudinally extending portion 320, longitudinally extending struts 325, 330 are circumferentially offset with respect to each other and are interconnected by a connecting portion 335. Connecting portion 335 contains at least one apex 340.

Adjacent pairs of longitudinally extending portions 320 are arranged in a specific manner. More particularly, circumferentially spaced pairs of longitudinally extending portions 320 are arranged so that a pair of a longitudinally extending struts 330 are spaced at a first distance C and a pair of longitudinally extending struts 325 are spaced at a distance D. As shown, distance C is greater than distance D.

When stent 300 is bent (FIG. 9), it generally maintains its tubular configuration—i.e., the conformability of stent 300 is quite good. The poor conformability and kinking problem described above with respect to stent 200 in FIGS. 4-5 and stent 400 in FIG. 6 is reduced or avoided. In addition, the crashing and out of tubular configuration problem described above with respect to stent 100 in FIGS. 1-3 is reduced or avoided. This is primarily due to the design of longitudinally extending portions 320 and the orientation of circumferentially adjacent pairs of longitudinally extending portions 320 (as discussed above), which allows for necessary expansion when stent 300 is placed under tension and contraction when stent 300 is placed under compression. These longitudinal tension and compression forces are experienced when the stent 200 is placed on a curve as show in FIG. 9. FIGS. 10-12 show in detail how the longitudinally extending portions allow for this expansion and contraction.

Thus, stent 300 provides a combination of advantages that is not seen as such with stent 100 in FIGS. 1-3 or stent 200 in FIGS. 4-5 or stent 400 in FIG. 6.

FIG. 11 illustrates stent 300 in a neutral configuration—i.e., there are no stresses placed on the stent. In this configuration, peaks 345, 350 in an adjacent pair of longitudinally adjacent circumferential rings 310 are spaced at a first distance E. When stent 300 is placed under tension (which occurs along the larger radius of a bend) (FIG. 10), longitudinally adjacent peaks 345, 350 of a longitudinally adjacent pair of circumferential rings 310 are longitudinally spaced at a distance F that is greater than E in FIG. 11. As is also apparent from FIG. 10, the distance between circumferentially adjacent pairs of apices 340 in longitudinally extending portions 320 increases when stent 300 is placed under longitudinal tension.

With reference to FIG. 12, it can be seen that when stent 300 is placed under compression (which occurs along the smaller radius of a bend), longitudinally adjacent peaks 345, 350 in a longitudinally adjacent pair of circumferential rings 310 are spaced at a distance G which is less than distance E in the neutral configuration of stent 300 (FIG. 11). In addition, it can be seen that the distance between circumferentially adjacent pairs of apices 340 in adjacent longitudinally extending portions 320 generally decreases when stent 300 is placed under longitudinal compression.

This dynamic behaviour of the longitudinal connectors 320 when the stent is placed under compression or tension can be regarded as a pivoting action which improves the flexibility and conformability of stent 300 while minimizing or reducing having struts in the stent to contact or crash on each other. This advantage is also illustrated in FIG. 8 which shows stent 300 on a curve.

Figure 13:
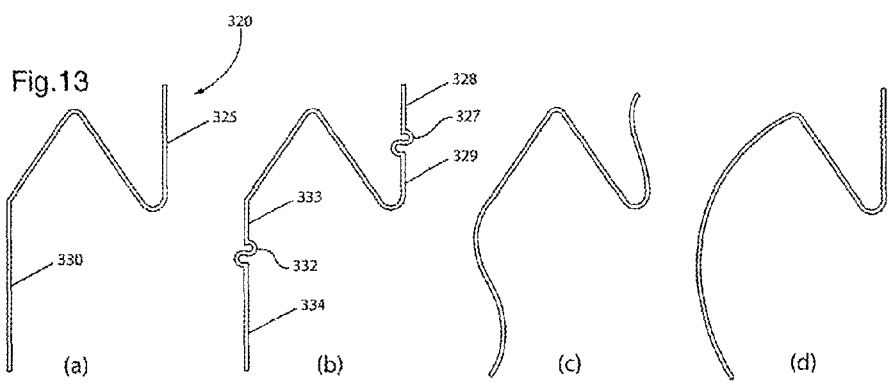
FIGS. 13-15 illustrate various alternate embodiments of the longitudinally extending portion used in the stent design shown in FIGS. 7-9.
Figure 14:
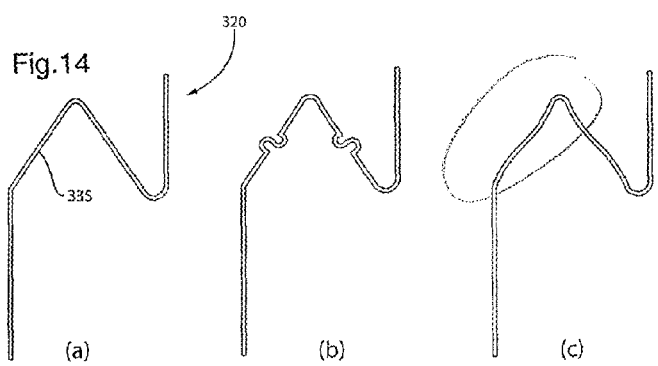
Figure 15:
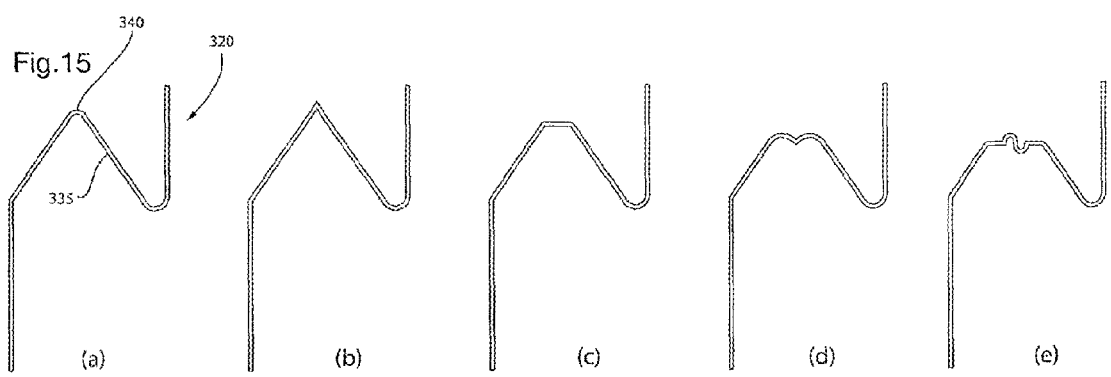

With reference to FIGS. 13-15, there is illustrated a series of alternatives to longitudinally extending portions 320 illustrated in FIGS. 7-12.

Thus, in FIG. 13(*a*), longitudinally extending portion 320 is illustrated as a starting point for modification. In FIGS. 13(*b*) through 13(*d*), there is shown modifications to longitudinally extending struts 325, 330. In FIG. 13(*b*), longitudinally extending strut 325 is modified to include a curved flex member 327 that is located between a pair of straight portions 328 and 329. Summarily, longitudinally extending strut 330 has been modified to include a curved flex member 332 that is located between a pair of straight sections 333 and 334.

While flex members 327, 332 in FIG. 13(*b*) are depicted as S-shaped portions, it will be appreciated by those of skill in the art that the specific nature of the curved flex member may be modified and includes the various shapes of "flexure means" described and illustrated in U.S. Pat. No. 6,858,037 [Penn et al. (Penn)].

In FIG. 13(*c*), longitudinally extending struts 325, 330 have been modified such that each are substantially completely curved. In the illustrated embodiment, the struts have been modified to have a general S-shape. Of course, other curved shapes can be used.

In FIG. 13(*d*), only strut 330 has been modified and it has a general C-shape, wherein there is no distinguishable transition between struts 330 and connecting portion 335.

In FIGS. 14(*b*) and 14(*c*), there are illustrated modifications to connecting portion 335 of longitudinally extending portion 320 to include curved portions that are shown in FIGS. 13(*b*) and 13(*c*), respectively. In FIGS. 15(*b*) through 15(*e*), there are illustrated modifications to apex 340 of longitudinal extending portion 320.

Thus, in FIG. 15(*b*), the apex of connecting portion 335 has been modified to be pointed. In FIG. 15(*c*), this apex is flat. In FIG. 15(*d*), this apex has been modified to have a pair of curved portions with a dimple in between. Finally, in FIG. 15(*e*), the apex has been modified to have a flat portion with a curved flex member disposed therein.

Those of skill in the art will recognize it is possible to modify longitudinally extending portion 320 to include one or more of the features described in FIGS. 13-15. That is, it is possible to combine the various modifications shown in FIGS. 13-15 in a single longitudinally extending portion 320. Further, it is possible to modify the connecting portion between circumferential ring 310 and longitudinally extending portion 320 to have an apex similar to apex 340 comprised in connecting portion 320.

In addition to the above stated advantages associated with stent 300, there is a further advantage. Specifically, stent 300, having circumferential rings 310 of similar profile and amplitude, can be readily crimped while reducing or avoiding pre-deployment crashing of the various struts in the design. This can be seen with reference to FIG. 16.

The stent of the present invention may further comprise a coating material thereon. The coating material can be disposed continuously or discontinuously on the surface of the stent. Further, the coating may be disposed on the interior and/or the exterior surface(s) of the stent. The coating material can be one or more of a biologically inert material (e.g., to reduce the thrombogenicity of the stent), a medicinal composition which leaches into the wall of the body passageway after implantation (e.g., to provide anticoagulant action, to deliver a pharmaceutical to the body passageway and the like) and the like.

The stent is preferably provided with a biocompatible coating, in order of minimize adverse interaction with the walls of the body vessel and/or with the liquid, usually blood, flowing through the vessel. A number of such coatings are known in the art. The coating is preferably a polymeric material, which is generally provided by applying to the stent a solution or dispersion of preformed polymer in a solvent and removing the solvent. Non-polymeric coating materials may alternatively be used. Suitable coating materials, for instance polymers, may be polytetraflouroethylene or silicone rubbers, or polyurethanes which are known to be biocompatible. Preferably, however, the polymer has zwitterionic pendant groups, generally ammonium phosphate ester groups, for instance phosphoryl choline groups or analogues thereof.

Examples of suitable polymers are described in International application number WO-A-93/16479 and WO-A-93/15775. Polymers described in those specifications are hemocompatible as well as generally biocompatible and, in addition, are lubricious. It is important to ensure that the surfaces of the stent are completely coated in order to minimize unfavourable interactions, for instance with blood, which might lead to thrombosis. This good coating can be achieved by suitable selection of coating conditions, such as coating solution viscosity, coating technique and/or solvent removal step.

In another embodiment of the invention, the stent may be joined to a cover material to form a so-called stent graft. The cover may be a polymer or non-polymer material and it may be natural or synthetic. Non-limiting examples of suitable covering materials include bovine, basilic vein or other natural tissue, PTFE, e-PTFE, polyurethane, Gortex™, bioabsorbable materials and the like. The cover material may be secured to the inside or the outside of the stent. Of course, it is also possible to form a laminate construction wherein a pair of cover materials (similar or dissimilar) sandwich or otherwise surround at least a portion of the stent. The cover material may be secured to the stent by bonding, suturing, adhesion, mechanical fixation or any combination of these. Further, if the cover material is a polymer material, it may be extruded onto the stent in such a manner that it envelops at least a portion of the stent. This technique may be used to join two or more stents with a flexible polymeric tube. This technique may also be used to join a stent to another prosthetic device such as a tube, a graft and the like. Thus, in this embodiment of the invention, the stent is incorporated into an endoluminal prosthesis. The cover materials may fully or partially cover the stent in the radial and/or circumferential direction.

The manner by which the present stent is manufactured is not particularly restricted. Preferably, the stent is produced by laser cutting techniques applied to a tubular starting material. Thus, the starting material could be a thin tube of a metal or alloy (non-limiting examples include stainless steel, titanium, tantalum, nitinol, Elgiloy, NP35N, cobalt-chromium alloy and mixtures thereof) which would then have sections thereof cut out to provide a stent having a pre-determined design.

Thus, the preferred design of the present stent is one of a tubular wall which is distinct from prior art wire mesh designs wherein wire is conformed to the desired shape and welded in place. The preferred tubular wall design of the present stent facilitates production and improves quality control by avoiding the use of welds and, instead, utilizing specific cutting techniques.

In one embodiment, the present stent is configured to be a balloon expandable stent. In this embodiment, the stent can be made from a balloon expandable material such as stainless steel, titanium, tantalum, nitinol (certain grades), Elgiloy, NP35N, cobalt-chromium alloy and the like. The present stent may be implanted using a conventional system wherein a guidewire, catheter and balloon can be used to position and expand the stent. Implantation of mono-tubular stents such as this stent is conventional and within the purview of a person skilled in the art. See, for example, any one of U.S. Pat. Nos. 4,733,665, 4,739,762, 5,035,706, 5,037,392, 5,102,417, 5,147,385, 5,282,824, 5,316,023 and any of the references cited therein or any of the references cited herein above. Alternatively, the present stent may be manufacture from non-metal (e.g., polymer) materials and/or materials that are bioabsorbable.

It will be apparent to those of skill in the art that implantation of stent of the present can be accomplished by various other means. For example, it is contemplated that the stent can be made of a suitable material which will expand when a certain temperature is reached. In this embodiment, the material may be a metal alloy (e.g., nitinol) capable of self-expansion at a temperature of at least about 20° C., preferably in the range of from about 20° C. to about 37° C. In this embodiment, the stent could be implanted using a conventional catheter and the radially outward force exerted on the stent would be generated within the stent itself. Further, the present stent can be designed to expand upon the application of mechanical forces other than those applied by a balloon/catheter. For example, it is possible to implant the present stent using a catheter equipped with a resisting sleeve or retaining membrane which may then be removed with the catheter once the stent is in position thereby allowing the stent to expand. Thus, in this example, the stent would be resiliently compressed and would self-expand once the compressive force (i.e., provided by the sleeve or membrane) is removed. This is known as a self-expanding stent. Additional details on this approach may be found in U.S. Pat. Nos. 5,067,957 and 6,306,141.

Finally, it is preferred to incorporate one or more radioopaque markers in the present stent to facilitate view thereof during angiography typically used to guide the device to its intended location in the patient. It is particularly preferred to have at least one radioopaque marker at or near each of the proximal and distal ends of the stent. The material used as the radioopaque marker is preferably selected from the group consisting of gold, platinum, iridium, tantalum and tungsten.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A stent in an expanded-state and neutral configuration comprising:
　a plurality of undulating circumferential portions, each circumferential portion comprising alternating peaks and valleys; and
　a plurality of longitudinally extending portions connecting the plurality of undulating circumferential portions; wherein:
　(i) each of the plurality of longitudinally extending portions comprising a first longitudinally extending strut and a second longitudinally extending strut circumferentially offset with respect to the first longitudinally extending strut, the first longitudinally extending strut and the second longitudinally extending strut being interconnected by a connecting portion, the connecting portion comprising a first strut segment connected to the first longitudinally extending strut and a second strut segment connected to the second longitudinally extending strut, the first strut segment and the second strut segment are interconnected to define a single connecting apex therebetween;

(ii) a pair of circumferentially adjacent first longitudinally extending struts in a pair of circumferentially adjacent longitudinally extending portions are circumferentially spaced at a first distance and circumferentially adjacent second longitudinally extending struts in the pair of circumferentially adjacent longitudinally extending portions are circumferentially spaced at a second distance, the first distance being greater than the second distance; and (iii) circumferentially spaced connection portions being configured such that the single connecting apex in each circumferentially spaced connection portion is interposed in alternating longitudinally aligned pairs of a peak and a valley in adjacent undulating circumferential portions.

2. The stent defined in claim 1, wherein a pair of the circumferentially adjacent longitudinally extending portions, in two dimensions, is configured to be substantially mirror images of one another along a longitudinal axis of the stent.

3. The stent defined in claim 1, wherein a pair of the circumferentially adjacent longitudinally extending portions, in two dimensions, is configured to be substantially non-superimposable mirror images of one another along a longitudinal axis of the stent.

4. The stent defined in claim 1, wherein the first distance corresponds to a first section of a first undulating circumferential portion and the second distance corresponds to a second section of a second undulating circumferential portion adjacent to the first undulating circumferential portion, the first section and the second section having a different number of peaks and valleys.

5. The stent defined in claim 1, wherein each of the first strut portion and the second strut portion comprise a straight portion.

6. The stent defined in claim 1, wherein the at least one apex comprises a curved portion.

7. The stent defined in claim 1, wherein the first strut portion and the second strut portion are substantially mirror images of one another along a longitudinal axis of the stent.

8. The stent defined in claim 1, wherein the first longitudinally extending strut is connected to a valley of a first undulating circumferential portion and the second longitudinally extending strut is connected to a peak of a second undulating circumferential portion adjacent to the first undulating circumferential portion.

9. The stent defined in claim 1, comprising an even number of longitudinally extending portions interconnecting adjacent circumferential portions.

10. The stent defined in claim 1, wherein the ratio of the number peaks in each of an adjacent pair of circumferential portions to the number of longitudinally extending portions connecting the pair is 2:1.

11. The stent defined in claim 1, containing 4 longitudinally extending portions interconnecting an adjacent pair of circumferential portions.

12. The stent defined in claim 11, wherein each of the pair of circumferential portions has 8 peaks.

13. The stent defined in claim 11, having a diameter of less than or equal to about 30 mm.

14. The stent defined in claim 1, containing 6 longitudinally extending portions interconnecting an adjacent pair of circumferential portions.

15. The stent defined in claim 14, wherein each of the pair of circumferential portions has 12 peaks.

16. The stent defined in claim 14, having a diameter of greater than about 30 mm.

17. A stent in an expanded-state and neutral configuration comprising:
a plurality of undulating circumferential portions, each circumferential portion comprising alternating peaks and valleys; and
a plurality of longitudinally extending portions connecting the plurality of undulating circumferential portions;
wherein:
(i) each of the plurality of longitudinally extending portions comprising a first longitudinally extending strut and a second longitudinally extending strut circumferentially offset with respect to the first longitudinally extending strut, the first longitudinally extending strut and the second longitudinally extending strut being interconnected by a connecting portion;
(ii) a pair of circumferentially adjacent first longitudinally extending struts in a pair of circumferentially adjacent longitudinally extending portions are circumferentially spaced at a first distance and circumferentially adjacent second longitudinally extending struts in the pair of circumferentially adjacent longitudinally extending portions are circumferentially spaced at a second distance, the first distance being greater than the second distance; and
(iii) the ratio of the number peaks in each of an adjacent pair of circumferential portions to the number of longitudinally extending portions connecting the pair is 2:1.

18. A stent in an expanded-state and neutral configuration comprising:
a plurality of undulating circumferential portions, each circumferential portion comprising alternating peaks and valleys; and
a plurality of longitudinally extending portions connecting the plurality of undulating circumferential portions;
wherein:
(i) each of the plurality of longitudinally extending portions comprising a first longitudinally extending strut and a second longitudinally extending strut circumferentially offset with respect to the first longitudinally extending strut, the first longitudinally extending strut and the second longitudinally extending strut being interconnected by a connecting portion, the connecting portion comprising a first strut segment connected to the first longitudinally extending strut and a second strut segment connected to the second longitudinally extending strut, the first strut segment and the second strut segment are interconnected to define a single connecting apex therebetween;
(ii) a pair of circumferentially adjacent first longitudinally extending struts in a pair of circumferentially adjacent longitudinally extending portions are circumferentially spaced at a first distance and circumferentially adjacent second longitudinally extending struts in the pair of circumferentially adjacent longitudinally extending portions are circumferentially spaced at a second distance, the first distance being greater than the second distance; and
(iii) the longitudinally extending portions are the only connectors between longitudinally adjacent pairs of undulating circumferential portions.

19. The stent defined in claim 17, wherein: (i) the connecting portion comprising a first strut segment connected to the first longitudinally extending strut and a second strut segment connected to the second longitudinally extending strut, the first strut segment and the second strut segment are interconnected to define a single connecting apex therebetween, and (ii) circumferentially spaced connection portions being configured such that the single connecting apex in each circumferentially spaced connection portion is interposed in alternating longitudinally aligned pairs of a peak and a valley in adjacent undulating circumferential portions.

20. The stent defined in claim 18, wherein circumferentially spaced connection portions being configured such that the single connecting apex in each circumferentially spaced connection portion is interposed in alternating longitudinally aligned pairs of a peak and a valley in adjacent undulating circumferential portions.

* * * * *